United States Patent [19]

Vinegar et al.

[11] Patent Number: 4,884,455

[45] Date of Patent: Dec. 5, 1989

[54] METHOD FOR ANALYSIS OF FAILURE OF MATERIAL EMPLOYING IMAGING

[75] Inventors: Harold J. Vinegar; Scott L. Wellington, both of Houston, Tex.; Jannetje A. de Waal, Rijswijk, Netherlands

[73] Assignee: Shell Oil Company, Houston, Tex.

[21] Appl. No.: 304,751

[22] Filed: Jan. 31, 1989

Related U.S. Application Data

[62] Division of Ser. No. 66,179, Jun. 25, 1987, Pat. No. 4,856,341.

[51] Int. Cl.$^4$ .............................................. G01N 3/00
[52] U.S. Cl. ........................................ 73/798; 73/153

[58] Field of Search ................... 73/798, 153; 378/8, 378/20, 21; 324/300

[56] References Cited

U.S. PATENT DOCUMENTS 4,564,811  1/1986  Walker ........................... 324/300 X
4,710,946  12/1987  Hinch et al. ...................... 73/153 X Primary Examiner—Jerry W. Myracle

[57] ABSTRACT

Methods are provided for determining mechanical and petrophysical properties (density, porosity, bulk compressibility, Young's modulus, Poisson's Ratio) of a material undergoing mechanical deformation studies with an imaging (CT, NMR) apparatus. The methods may also be used to measure and depict any fractures in the material.

12 Claims, 7 Drawing Sheets

A. ZERO PRESSURE
B. HYDROSTATIC PRESSURE 1000 psi
C. PRE-FRACTURE 8450 psi
D. POST-FRACTURE 2825 psi

METHOD FOR ANALYSIS OF FAILURE OF MATERIAL EMPLOYING IMAGING

This is a division of application Ser. No. 066,179 filed June 25, 1987, now U.S. Pat. No. 4,856,341.

BACKGROUND OF THE INVENTION

This invention relates to imaging of materials by X-ray Computed Tomography (CT) and Nuclear Magnetic Resonance Imaging (NMRI), and more particularly, relates to imaging of materials to determine mechanical and petrophysical properties of such materials.

Traditional studies of rock compaction have used measurements of fluid expulsion and axial shortening of a sample to measure compaction and dilation behavior of such a sample. Athough much can be learned from these measurements of average bulk properties of a sample, they do not reveal how physical properties vary spatially within a sample. Laboratory measurements of rock properties may result in nonuniform compaction throughout a sample, so that the average strain at which a sample fails may be considerably different from the local strain at the location of any first failure.

Moreover, many rock samples are intrinsically heterogeneous, even on a small scale, and the behavior in each such region of the sample may be of interest. For example, in studies of the compaction of turbidite earth formations, the turbidites are composed of thinly laminated and interbedded sands and shale having an overall thickness of from a few millimeters up to a few feet. Measurement of the separate bulk compressibilities and Poisson's ratios of the sands and the shales in the turbidite sequence is necessary because any hydrocarbons are normally contained only in the sand fraction of a turbidite reservoir.

In other mechanical deformation studies, there may be a large local variation in sample properties combined with the need to be able to make non-invasive measurements without altering the sample. An example of such a study is brittle failure in unconsolidated sands, where the sample cannot be removed from its compaction cell to examine any fracture after brittle failure because the sample becomes unconsolidated without confining stress.

Such mechanical deformation studies may generally be conducted to determine the strength of a particular material. For petrophysical applications, such studies may be employed to determine reservoir subsidence or compaction characteristics and thus aid in the design of production platforms or any recovery process used at a particular location of a reservoir.

There exists, therefore, an unfulfilled need to make local, non-invasive measurements of the mechanical properties of a sample, such as bulk compressibility and Poisson's ratio, and to study failure mechanisms for such samples without removing the sample from mechanical deformation apparatus.

These and other limitations and disadvantages of the prior art are overcome by the present invention and methods are provided for studying in a non-destructive manner the local changes in mechanical and petrophysical properties during material deformation.

SUMMARY OF THE INVENTION

In a preferred embodiment of the present invention, X-ray CT is employed to provide spatial information about changes in mechanical and petrophysical properties of samples, such as rock samples, undergoing testing for mechanical deformation.

X-ray CT is a powerful non-destructive technique that has been found to be useful in mechanical deformation studies to examine local changes in mechanical and petrophysical properties of a sample. The noninvasive nature of CT makes mechanical deformation studies possible at extreme conditions, such as at highly elevated temperatures or at cryogenic temperatures.

The methods of the present invention may be employed to determine various mechanical and petrophysical properties of a sample undergoing mechanical deformation. For compaction analysis, the preferred method applies uniaxial strain or hydrostatic pressure to a sample in measured or known preselected increments, with X-ray CT imaging of the sample occurring before and after each change in pressure. From these images, bulk density, porosity, bulk compressibility and Young's modulus may be determined. The sample may then be subjected to uniaxial forces that change in known preselected increments, with X-ray CT imaging of the sample occurring before and after any such uniaxial force changes. From these images, and the properties determined from the hydrostatic pressure changes, Poisson's ratio and Lamé parameters may be determined. The methods of the present invention may also be employed during tensile deformation of a sample.

Alternatively, NMR Imaging may be employed to image fluids in a sample to provide spatial information about pore volume changes in samples undergoing mechanical deformation testing. When X-ray CT is employed to image a material, the measurement of density, and density changes, may be as described in U.S. Pat. No. 4,571,491 issued Feb. 18, 1986, whose teachings are expressly incorporated herein by reference.

It is an object of the present invention to provide methods to make local, non-invasive measurements of mechanical properties of a sample.

It is also an object of the present invention to provide methods for determining mechanical and petrophysical properties of a material.

It is a specific object of the present invention to provide a method for determining at least one preselected property of a sample of material employing an imaging apparatus, comprising, imaging said sample during the application of known preselected forces to said sample and determining density in said sample responsive to said preselected forces.

These and other objects and advantages of the present invention will become apparent from the following detailed description, wherein reference is made to the Figures in the accompanying drawings.

Figure 5:
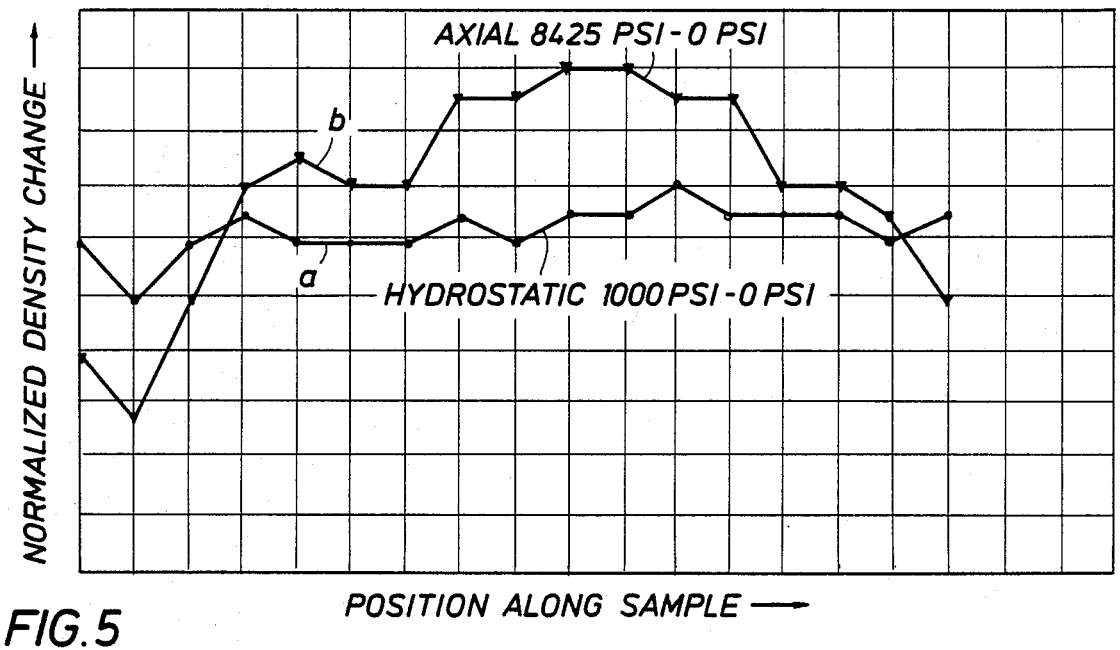
Figure 6:
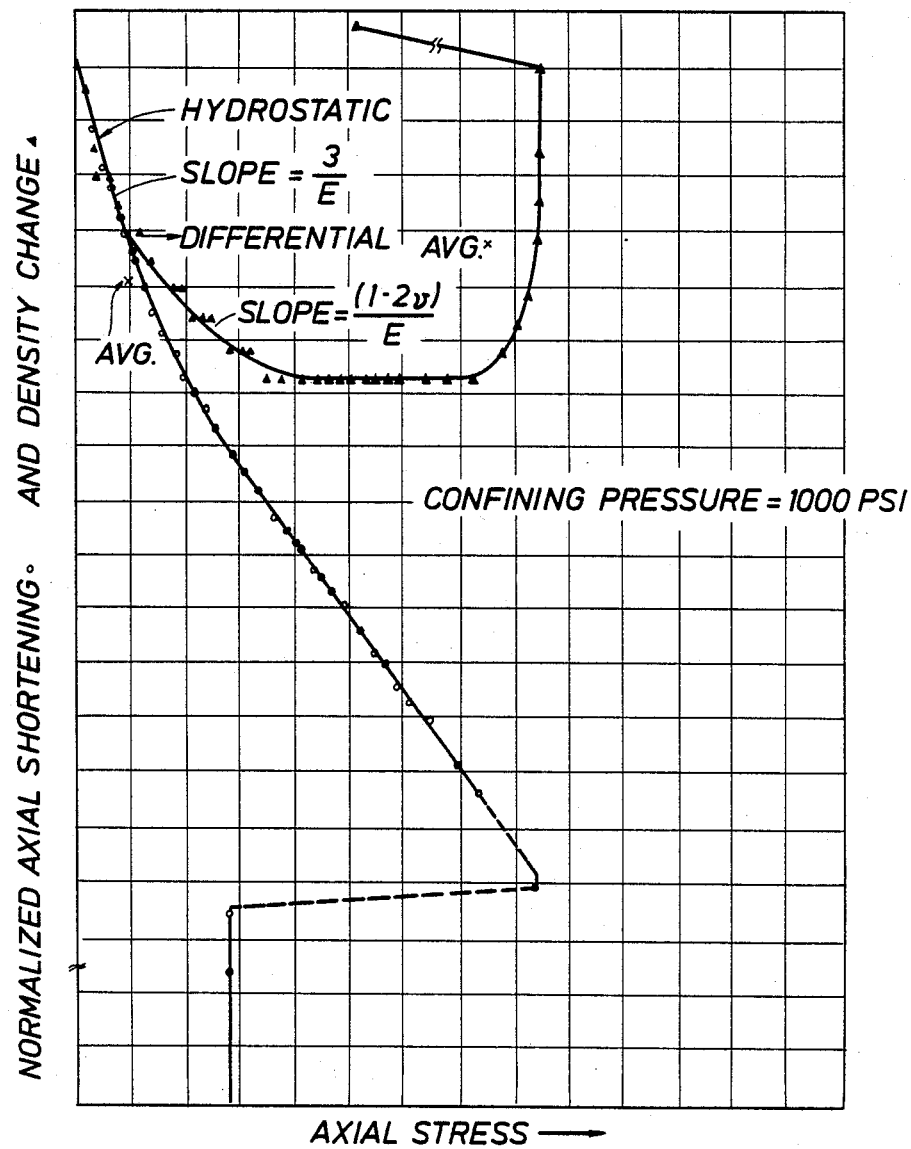
Figure 7:
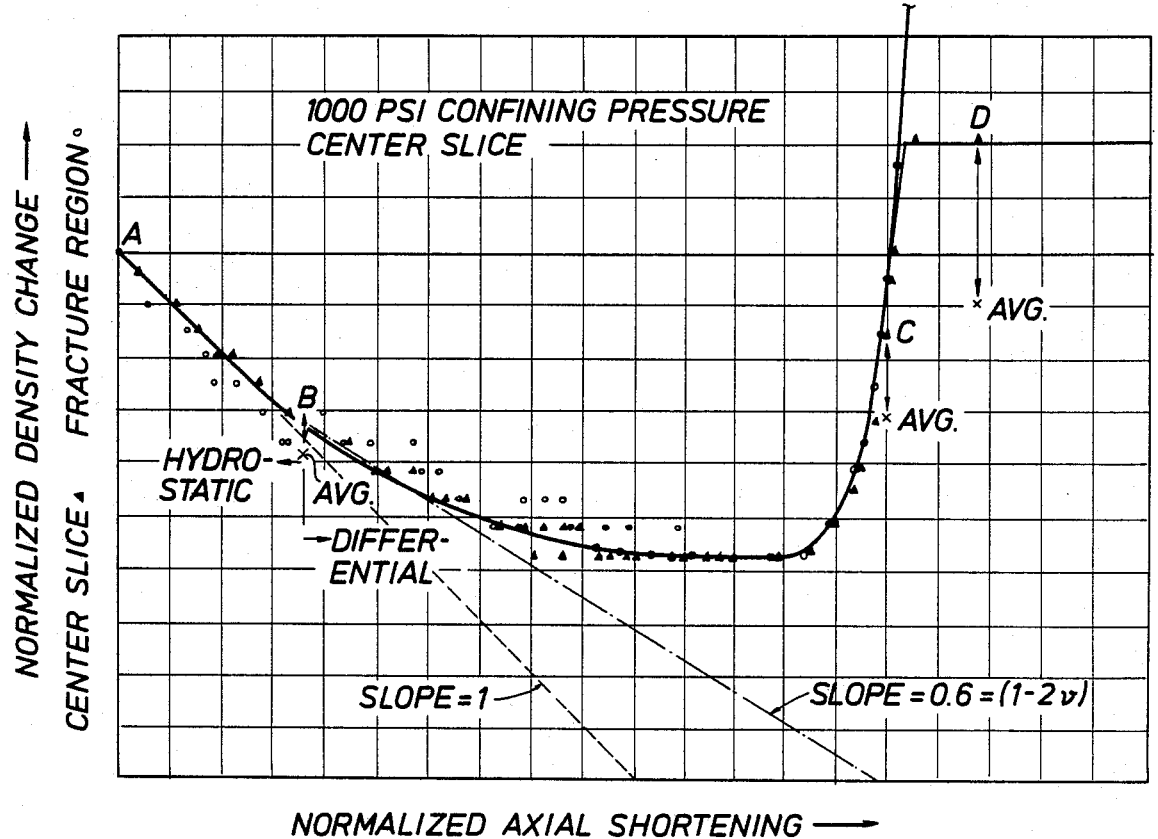
Figure 8:
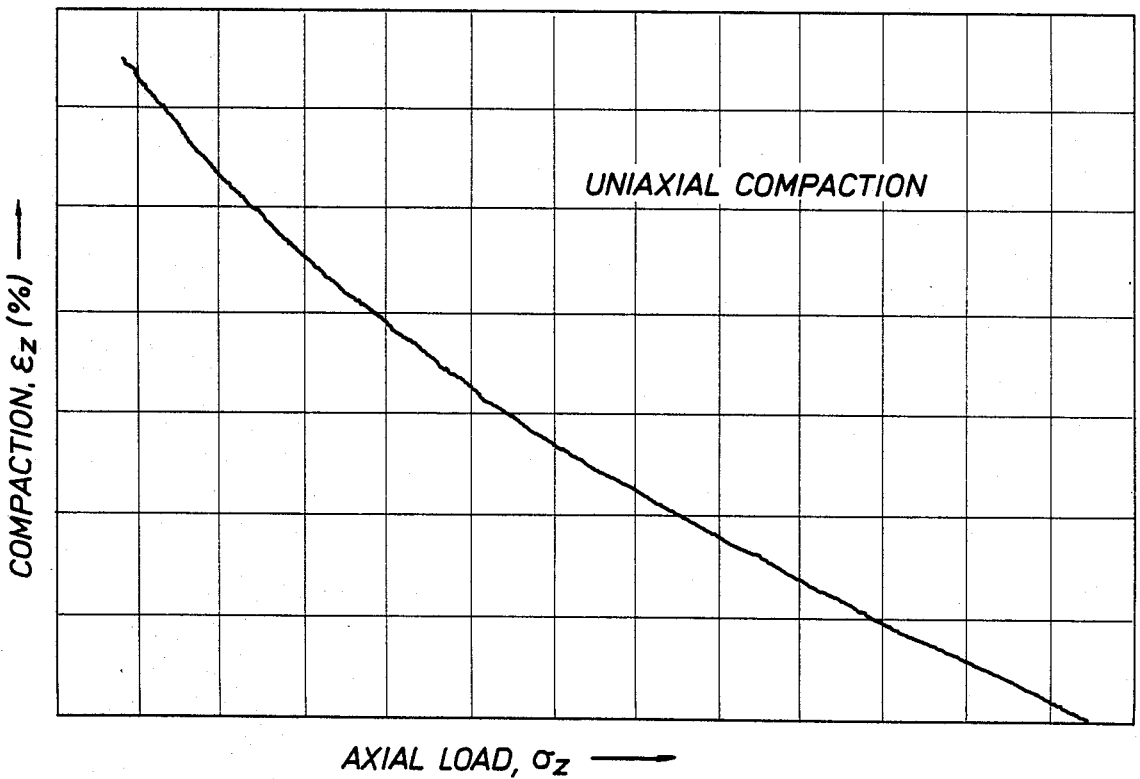

FIG. 5 depicts rock sample experimental data.
FIG. 6 depicts rock sample experimental data.
FIG. 7 depicts rock sample experimental data.
FIG. 8 depicts rock sample experimental data.

Figure 9:
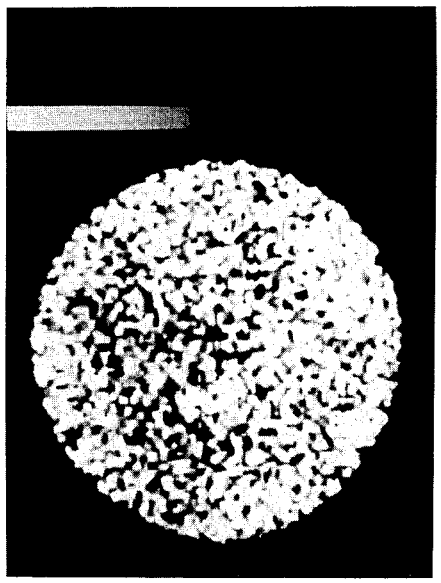
Figure 9:
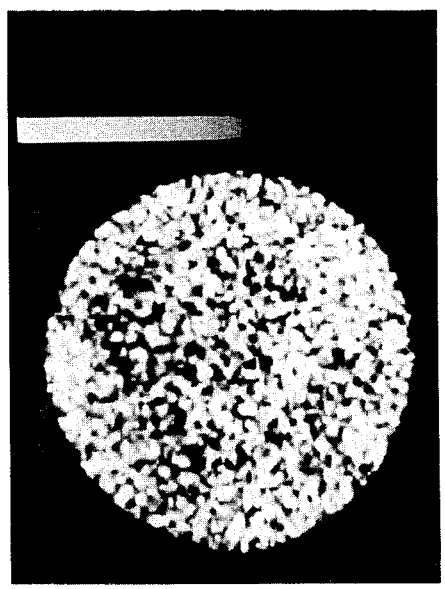
Figure 9:
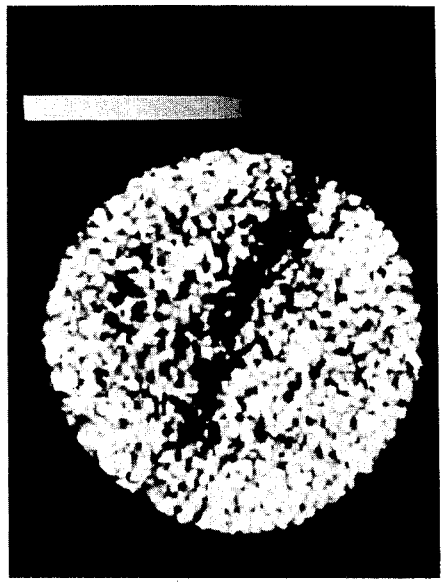
Figure 9:
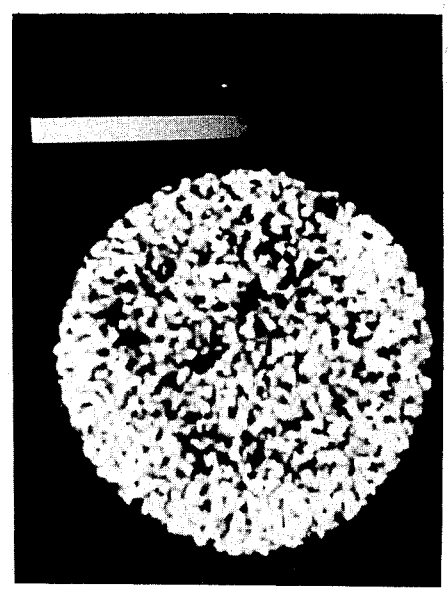
Figure 10:
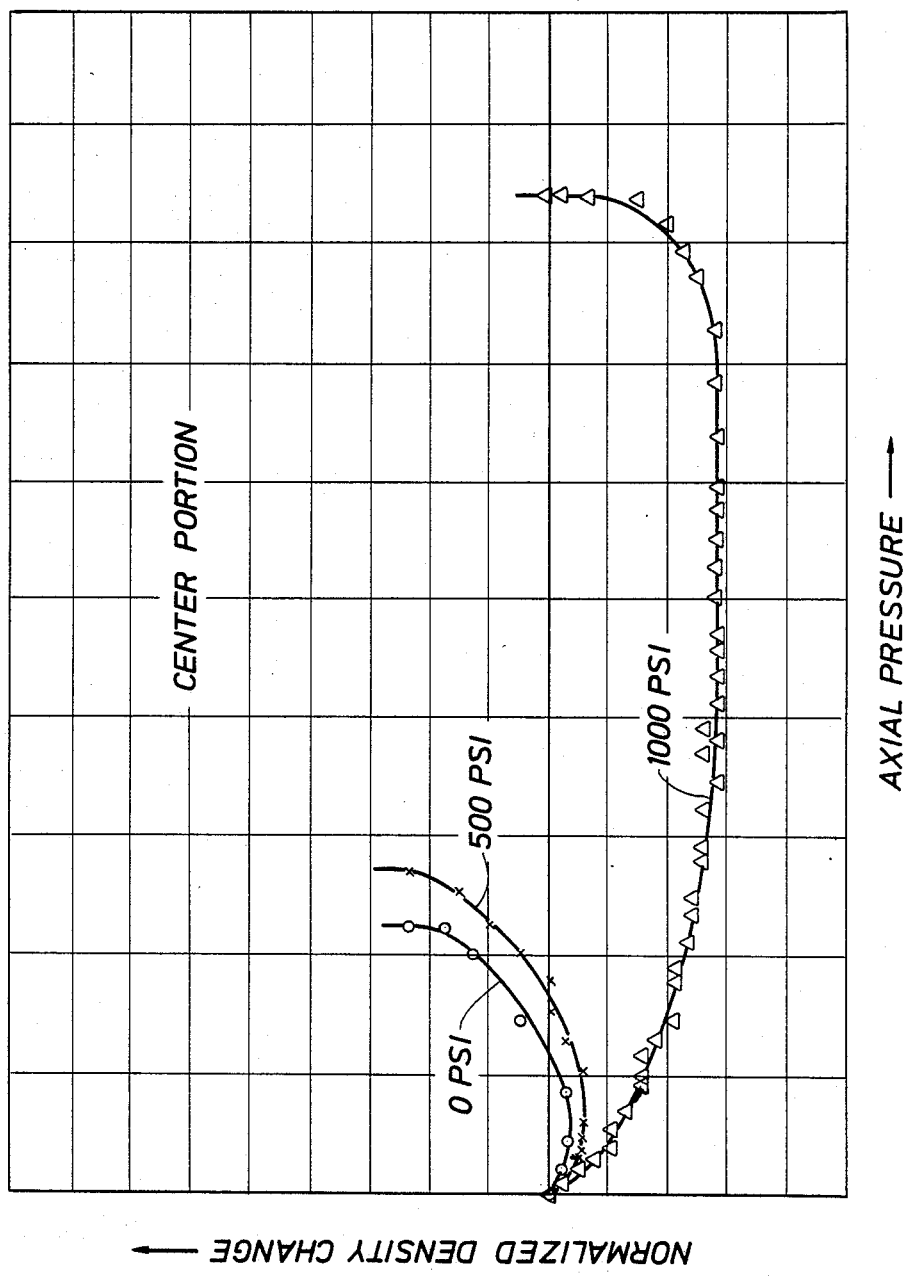

FIGS. 9 A-D depict rock sample experimental data.
FIG. 10 depicts rock sample experimental data.

DETAILED DESCRIPTION OF THE INVENTION

In a preferred embodiment of the present invention, X-ray CT is used to study density and density changes during known mechanical deformation of a sample, although in accordance with the methods of the present invention NMRI may be employed instead of X-ray CT. A brief summary of a CT scanner and an NMR imaging apparatus is presented herein for explanatory completeness.

Figure 1A:
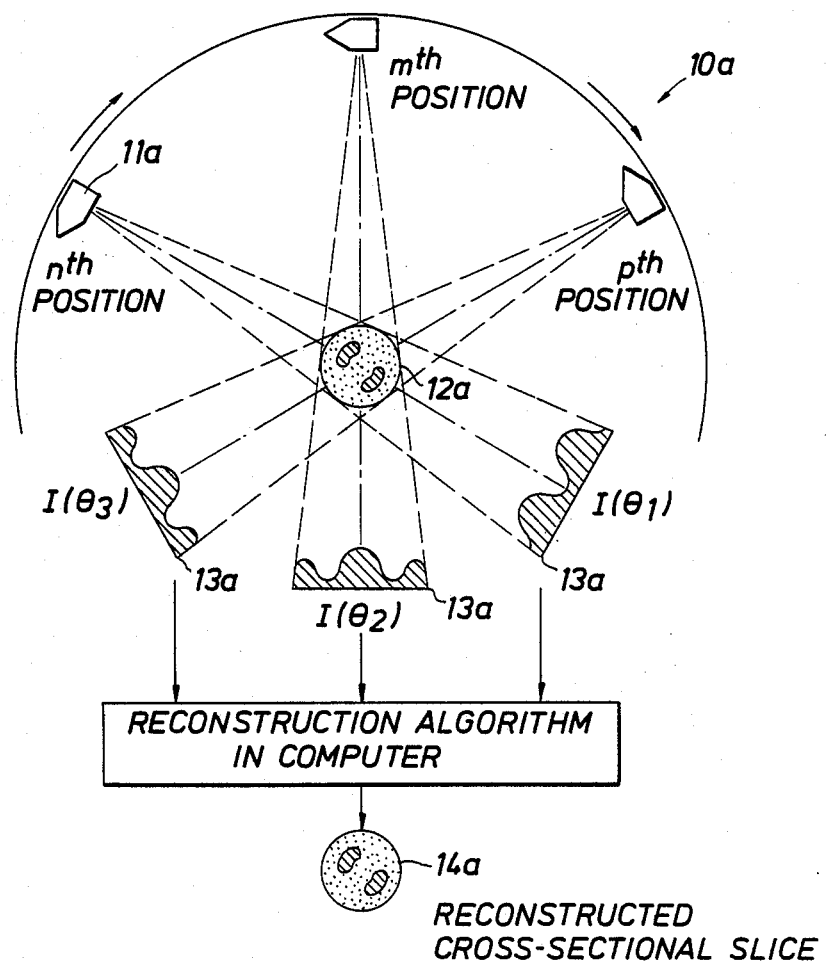
FIG. 1A depicts a simplified representation of an X-ray CT scanner.

Referring now to FIG. 1A, there may be seen a simplified representation of an X-ray CT scanner 10a. CT uses a collimated X-ray source 11a rotating at least 180° around an appropriate sample holder 12a containing a sample. At each angular position, a one-dimensional projection of X-ray attenuation 13a is obtained. From a set of these projections 13a, a cross-sectional slice 14a through the sample is later reconstructed by one of many available computer algorithms. A 3-dimensional image can then be reconstructed from sequential cross-sectional slices taken as the sample is moved through the scanner. The sample may be moved through the scanner by an appropriate sample table, such as that taught in U.S. Pat. No. 4,583,242, issued Apr. 15, 1986, whose teachings are expressly incorporated by reference herein.

Compared to an X-ray shadowgram, where attenuation from all irradiated planes through the object are superimposed, a CT image has excellent detectability of regions with small attenuation contrast. A 0.1% variation in X-ray attenuation can be measured over an area of 2 mm² or less.

A CT scanner measures a radiological quantity called the linear attenuation coefficient, $\mu$. For X-ray energies below about 1 MeV, $\mu$ consists only of contributions from Compton scattering and photoelectric absorption and may be written as, $$\mu = \rho(a + bZ^m/E^3) \quad (1)$$

where $\rho$ is the electron density, Z is the atomic number, E is the X-ray energy, a and b are approximately energy-independent coefficients, and m is a constant for each particular material and normally is in the range 3.0-4.0. In studies of compression or elongation of materials, or rock mechanics studies, all the quantities on the right side of equation (1) remain constant during the experiment except the density. Thus, any changes in attenuation coefficients are directly proportional to changes in bulk density. Absolute density measurements with a CT scanner require the use of two different X-ray energies; this technique is fully described in U.S Pat. No. 4,571,491, issued Feb. 18, 1986, whose teachings are incorporated herein by reference.

Figure 1B:
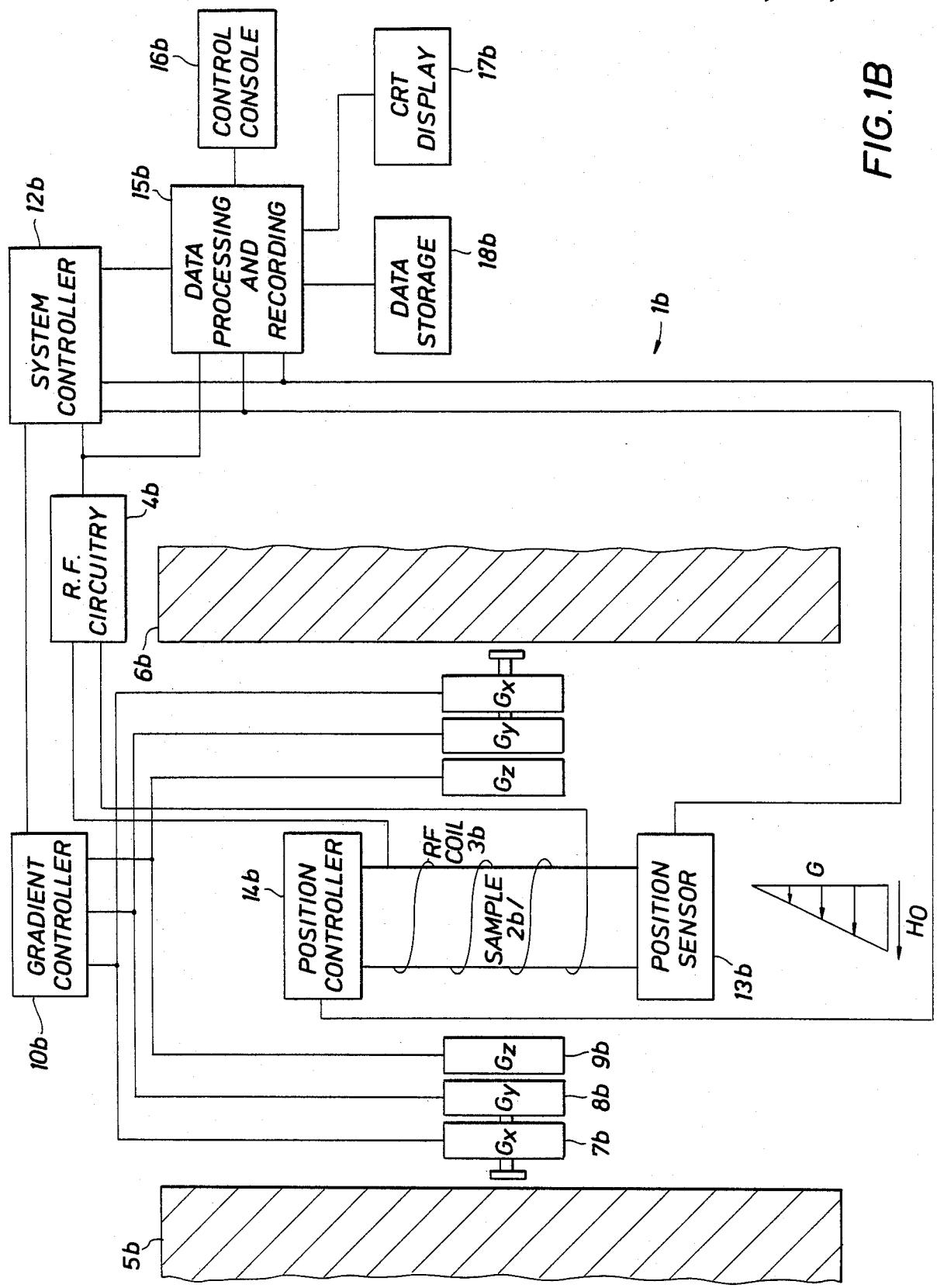
FIG. 1B depicts a simplified representation of an NMR Imaging Apparatus.

Referring now to FIG. 1B there may be seen a simplified functional drawing of an NMR imaging apparatus 1b suitable for practicing the methods of the present invention. In particular, FIG. 1B shows a sample 2b inside radio frequency coil 3b which is connected to radio frequency circuitry 4b. Sample 2b may also be contained in an appropriate sample holder (not shown for clarity). An essentially constant magnetic field $H_o$ is produced by poles 5b and 6b of a magnet, which may be a permanent magnet, an electromagnet, or a superconducting magnet. The main magnet field $H_o$ is preferably between 0.1-4.0 Tesla although both higher and lower field strengths may be successfully employed. The radio frequency coil 3b produces a radio frequency magnetic field $H_l$ which is perpendicular to $H_o$.

Gradient field coils 7b, 8b, 9b for x, y, and z directions, respectively, which are controlled by gradient controller 10b, may be employed to produce magnetic field gradients $G_x$, $G_y$, $G_z$, which may be spatially dependent linear gradients, appropriately oriented along the x, y, or z direction. The gradient controller 10b changes the gradient field electronically by varying the current to the gradient field coils.

System controller 12b controls the radio frequency circuitry 4b and gradient controller 10b. System controller 12b also receives data on the position of sample 2b through position sensor 13b and controls the position of the sample 2b with position controller 14b. System controller 12b also interfaces with data processing and recording means 15b. Data processing and recording means 15b receives data from the radio frequency circuitry 4b and position sensor 13b. Control console 16b, CRT display 17b, and data storage means 18b also interface with the data processing and recording means 15b. Such NMR Imaging apparatus are well known in the art and are described herein for explanatory purposes.

NMR imaging was first proposed by P. C. Lauterbur in *Nature*, Vol. 242, Mar. 16, 1973, pps. 190-191. In NMR imaging, a linear magnetic field gradient is applied to a sample so that the resonant frequencies of nuclear spins depend on the spatial location of those spins. The Fourier transform of the detected NMR spectrum represents the projection of the nuclear spin density $M_o$ perpendicular to the direction of the applied field gradient. A two- or three-dimensional image is constructed from a number of these projections at different angles. A comprehensive review of NMR imaging can be found in the book, *NMR Imaging In Biomedicine*, by P. Mansfield and P. B. Morris, Academic Press, 1982.

The preferred NMR imaging technique of the present invention is the Fourier spin-echo technique. However, other NMR imaging techniques may be employed in the methods of the present invention, such as for example, but not limited to projection reconstruction imaging, spin-warp imaging, etc. These and other imaging schemes are well known in the art of NMR imaging.

Practice of the methods of the present invention involves placing a sample 2b, or a sample in an appropriate sample holder (as noted later herein), in coil 3b and imaging a region of the sample, which may be a slice, plane, or volume of sample 2b. For NMR imaging the pore space of a solid sample must be 100% saturated with fluid, since NMR images only the fluid and not the solid matrix of the sample. However, if appropriate nuclei in a semi-solid material are sufficiently mobile, they may be directly imaged. When the spin-echo technique is employed in sedimentary rocks, the interpulse delay time, $\tau$, should be sufficiently short that the NMR signal is detected before it has significantly decayed from various relaxation mechanisms. For typical sedimentary rocks of interest in petroleum engineering, interpulse delay times below about 10 milliseconds have been found to be sufficiently short.

In studies of compression or elongation of materials, or rock mechanics studies, the NMR imaging apparatus measures the strength of the nuclear spin density $M_o$ signal from an appropriate fluid in the pore space of a sample, or other mobile nucleii, and changes in this signal reflect changes in fluid-filled pore space in the sample; thus the $M_o$ images correspond to changes in pore space as forces are applied to the sample and pore fluid is expelled from the sample. Typically, water is the pore fluid and the nuclear spin density $M_o$ of the proton is imaged, althought other nuclei may also be imaged.

While X-ray CT measures electron density of a sample, NMR measures the nuclear spin density of the fluid-filled pore space. Thus, $\Delta V/V = \Delta \rho/\rho = \emptyset \Delta M_o/M_o$, where V=bulk volume, $\rho$=bulk density, and $\emptyset$=porosity. Accordingly, fractional changes in bulk volume may be determined from imaging by measuring density ($\rho$) and density changes ($\Delta \rho$) with an X-ray CT scanner, or by measuring nuclear spin density ($M_o$) and nuclear spin density changes ($\Delta M_o$) with an NMR imaging apparatus. Porosity ($\emptyset$) is already known or is appropriately measured by an NMR imaging apparatus; such measurement may be as taught in U.S. patent application No. 765,406, filed Aug. 13, 1985, now U.S. Pat. No. 4,728,892, issued Mar. 1, 1988, whose teachings are expressly incoporated by reference herein. The term "density" is used herein to mean bulk density, electron density, and/or nuclear spin density.

Referring again to X-ray CT imaging, a modified medical CT scanner, as described in U.S. Pat. No. 4,571,491, was used to generate the examples described later herein; this scanner is basically a Deltascan 100 head scanner manufactured by Technicare Corporation. This scanner is a second-generation scanner with translate-rotate geometry and a 25 cm reconstruction circle. The scanner uses a tungsten target X-ray tube operated at a peak acceleration voltage of 120 KeV and has three bismuth germanate scintillation detectors. An image cross-section of 256 by 256 pixels is scanned for each slice and may be concurrently reconstructed in about two minutes. The thickness of each cross-sectional slice is a Gaussian shape of about 7 mm full-width at half-maximum.

For the CT scanner employed in the examples, as noted hereinabove, the CT images were stored on nine-track magnetic tape for archiving and post-processing analysis. In addition to the built-in CT display features, remote post-processing software such as zoom display may be employed in the methods of the present invention and was employed as noted later herein. Statistical averages of CT values and bulk density may be obtained in any large or small region of the sample (i.e. in a region as small as an individual pixel or up to a region as large as the entire sample).

For X-ray CT compaction experiments, the samples may be mounted inside an appropriate aluminum pressure vessel (described later herein) which is moved through the CT gantry on a sample table under computer control. The sample table of U.S. Pat. No. 4,583,242, referred to hereinbefore has a positioning accuracy of at least 0.0005 inches.

Figure 2:
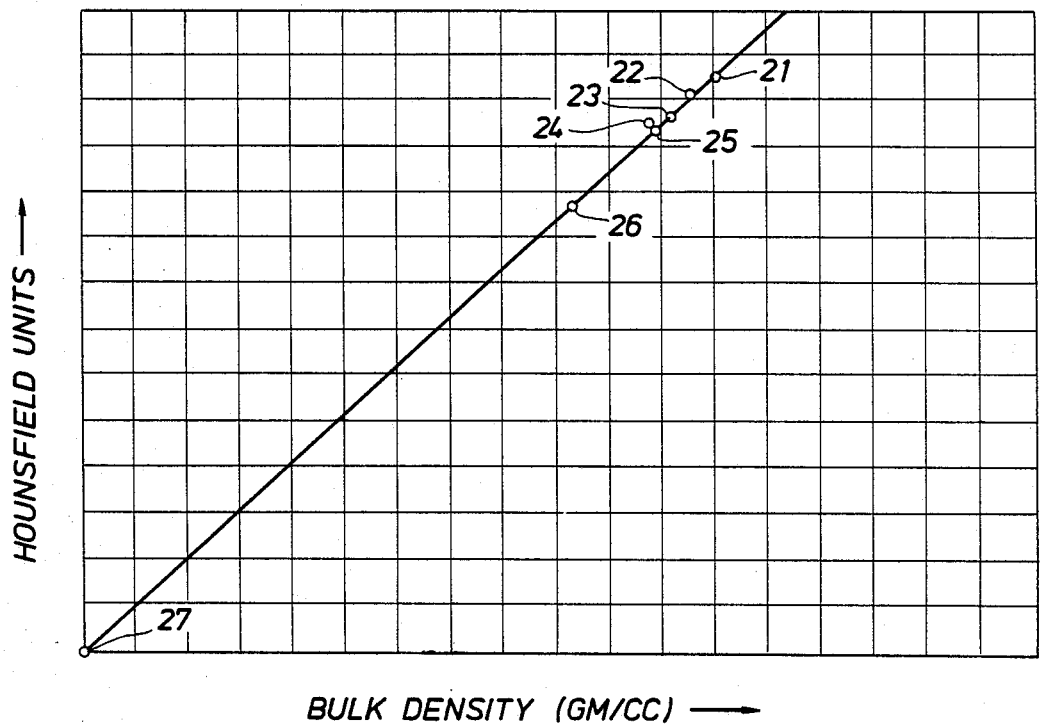
FIG. 2 depicts a CT calibration curve for rock materials.

CT medical data is normally presented in an internationally standardized scale called Hounsfield units (H) which are defined as $-1000$ H for air and 0 (zero) H for water. Thus, each H unit represents a 0.1% change in density, assuming all other terms in the linear attenuation coefficient are the same. Medical CT scanners are normally calibrated to this scale by scanning an acrylic waterbath and setting the observed water values to 0 H. However, for CT measurements of rock materials, such as sandstones, it is more convenient to calibrate using a $SiO_2$ standard such as fused quartz (bulk density=2.20 gm/cc). This results in a calibration curve shown in FIG. 2 which includes fused quartz 21, several sandstones 22-26, and air 27. From the slope of this curve, a change of $\pm 1$ H is equivalent to a normalized density change, $\Delta \rho/\rho$, of $0.5 \times 10^{-3}$ for sandstone materials. The bulk densities of sandstones 22-26 were independently determined by hydrostatic weighing in toluene and used to obtain this calibration curve.

Figure 3:
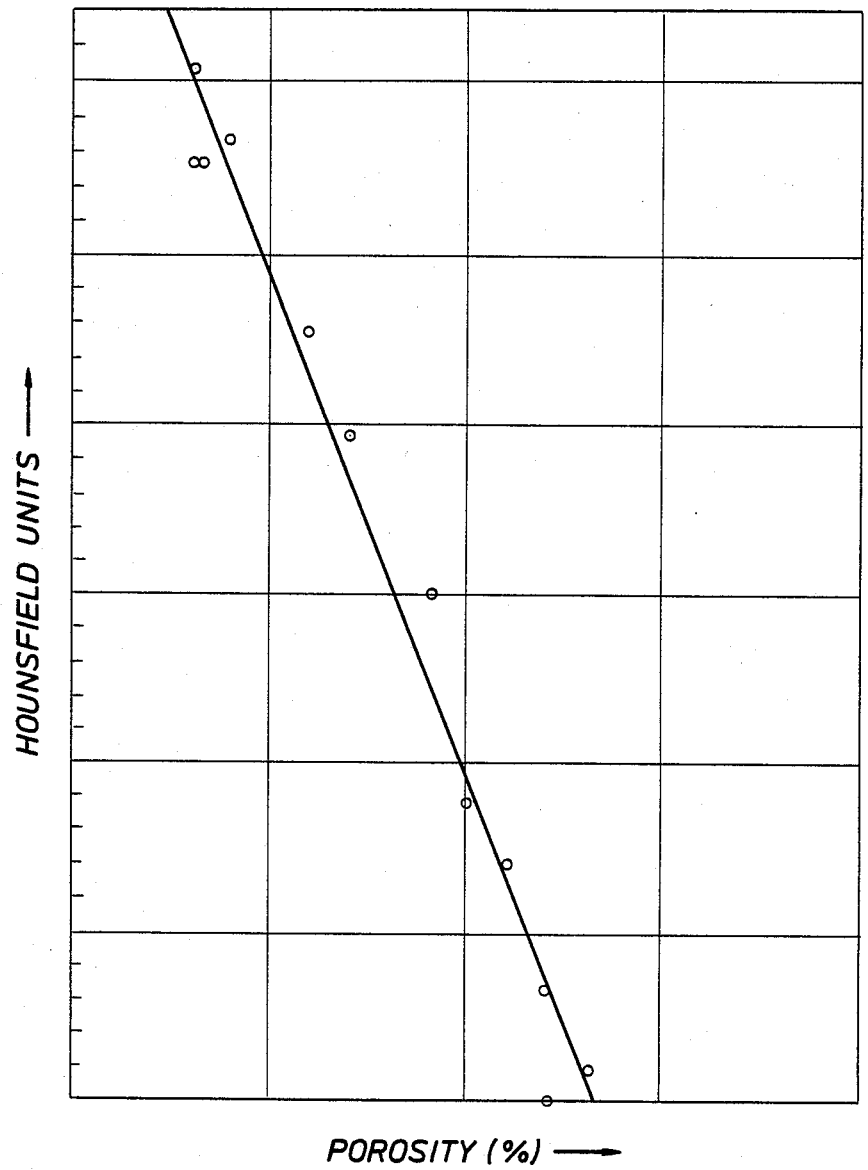
FIG. 3 depicts a curve of porosity versus density for typical rock material.

To illustrate the precision obtainable in CT measurements of bulk density and porosity, a dry Berea sandstone core, 2" o.d. by 12" long, was scanned every inch along its entire length. Three cross-sectional measurements were taken at each position of the sample and averaged. This same core was then sliced into twelve 1" sections and both the porosity and grain density of each section was measured by conventional hydrostatic weighing in toluene. The bulk density was computed from $\rho_b = (1-\emptyset)\rho_g$ where: $\rho_b$=bulk density, $\rho_g$=grain density, and $\emptyset$=porosity. The petrophysical and CT data is tabulated in Table I below, and FIG. 3 plots the linear relation observed between Hounsfield units and porosity for this sample. The standard error of estimation of porosity using the average CT data is $\pm 0.061$ porosity unit, which is comparable to the precision obtained with the conventional method of hydrostatic weighing in toluene. Thus, it can be seen that for a single grain type, there is a linear relationship between porosity and X-ray linear attenuation. Further, it can be seen that it is possible to calibrate the measured normalized density change and/or density to a corresponding bulk density change and/or bulk density, as noted hereinabove.

TABLE I

| Sample No. | Porosity % | Grain Density gm/cc | Bulk Density gm/cc | CT (H) Average of three readings |
| --- | --- | --- | --- | --- |
| 1 | 21.3 | 2.653 | 2.088 | 1073.0 |
| 2 | 21.3 | 2.654 | 2.089 | 1073.0 |
| 3 | 21.3 | 2.653 | 2.088 | 1075.6 |
| 4 | 21.4 | 2.653 | 2.085 | 1073.7 |
| 5 | 21.6 | 2.653 | 2.080 | 1068.6 |
| 6 | 21.7 | 2.653 | 2.077 | 1066.0 |
| 7 | 21.9 | 2.653 | 2.072 | 1061.7 |
| 8 | 22.0 | 2.653 | 2.069 | 1056.0 |
| 9 | 22.1 | 2.652 | 2.066 | 1054.3 |
| 10 | 22.2 | 2.652 | 2.063 | 1051.0 |
| 11 | 22.3 | 2.653 | 2.061 | 1049.0 |
| 12 | 22.2 | 2.653 | 2.064 | 1048.0 |

Figure 4:
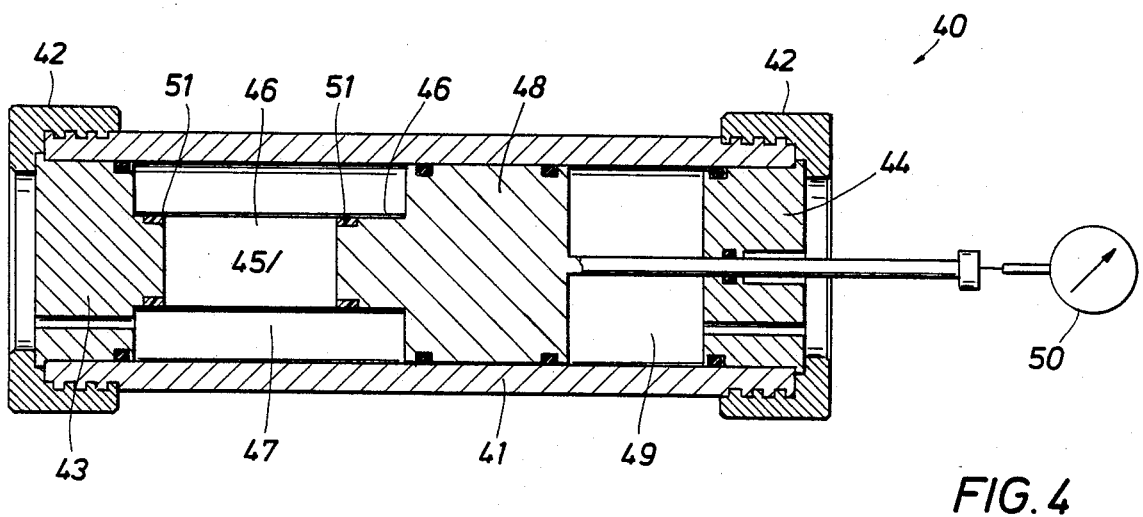
FIG. 4 depicts a pressure vessel employed to test rock samples under hydrostatic and non-hydrostatic stress conditions.

FIG. 4 shows a pressure vessel 40 which may be used to practice the methods of the present invention and was employed in the compaction measurements noted later herein. However, the methods of the present invention may also be employed for tensile measurements. The pressure vessel tube 41 is constructed of 7075 Aluminum for high tensile strength. End pieces 42 threadedly engage the ends of tube 41, and maintain pressure-retaining members 43, 44 in their proper positions at the ends of tube 41, via their oversize shoulders at one end. Each sample 45 is surrounded by a shrink-fit teflon sleeve 46 through which confining pressure is applied by fluid 47. Independent axial load is applied by means of movable piston 48, driven by fluid 49 and the axial strain on sample 45 is measured by dial gauge 50; alternatively, the axial strain may be measured by an appropriate transducer. Experiments may be performed both with and without TEFLON endpieces 51 to study the influence of sliding and fixed-end boundary conditions.

For NMR imaging, those portions of the sample holder inside the magnetic field and radio frequency coil should be constructed from non-metallic and nonferromagnetic components. Such a sample holder may be constructed in accordance with the teachings of copending U.S. patent application No. 066,176 filed on June 25, 1987, now U.S. Pat. No. 4,827,761.

In accordance with the methods of the present invention, the sample is placed in an appropriate sample holder, which is then placed in an imaging apparatus, which is preferably an X-ray scanner. The sample is initially hydrostatically raised to some pressure, $P_1$, (i.e. all parts of the sample subjected to the same pressure) at which it is desired to determine a sample's mechanical property. Most mechanical properties, such as bulk compressibility, have a value that is dependent upon the pressure at which the property is determined. The sample is then scanned or imaged in the region or regions of interest. The pressure on the sample is then hydrostatically increased some incremental pressure, $\Delta P$, and the sample is again scanned, as noted hereinbefore. For consolidated rock materials this $\Delta P$ should be more than about 200 PSI to ensure a sufficient change in density, or other property to be measured.

For homogeneous, isotropic samples under hydrostatic pressure, the three principal stresses are all equal, i.e. $\sigma_1 = \sigma_2 = \sigma_3 = 94$ and the principal strains $\epsilon_1 = \sigma_1/E$, $\epsilon_2 = \sigma_2/E$, $\epsilon_3 = \sigma_3/E$, are also equal, where E is Young's modulus. The fractional change in bulk volume and normalized density is therefore:

$$\frac{\Delta V}{V} = \frac{\Delta \rho}{\rho} = \frac{\emptyset \Delta M_o}{M_o} = \epsilon_1 + \epsilon_2 + \epsilon_3 = \frac{3\sigma}{E} \quad (2)$$

where $\rho$ is the average density measured by the CT scanner at $P_1$ and $P_1 + \Delta P$, and $\Delta \rho$ is the difference in density at these two force levels or pressures, and $\sigma$ is the change in measured pressure applied to the sample, which is preferably continuously measured during these operations. (For NMR applications, $\Delta V/V = \emptyset \Delta M_o/M_o$, with $M_o$ and $\Delta M_o$ determined in a manner analogous to $\rho$ and $\Delta \rho$ and $\emptyset$ is known porosity, and where grains and fluid in the pores are considered incompressible.) Bulk compressibility, $c_b$, is given by $$c_b = \frac{\Delta \rho/\rho}{\sigma} = \frac{\emptyset \Delta M_o/M_o}{\sigma} \quad (3)$$

where $\Delta \rho$ (or $\Delta M_o$) is the difference in density measured at $P_1$ and at $P_1 + \Delta P$, $\rho$ (or $M_o$) is the average of these density measurements, and $\sigma$ is the change in measured pressure during these measurements. When these experiments start at (or finish at) zero pressure, $c_b$ is an absolute value, otherwise it (and other properties so determined) is a differential measurement and value. Thus, Young's modulus may also be computed from measurements of bulk compressibility using:

$$E = \frac{3}{c_b} \quad (4)$$

Once the desired values of $c_b$ and/or E have been determined at the desired pressures, or pressure ranges, the sample may then be subjected to uniaxial stress to determine additional properties in conjunction with the already determined hydrostatic properties.

For uniaxial stress conditions, the three principal stresses are $\sigma_1 \neq 0$, $\sigma_2 = 0$, $\sigma_3 = 0$, and the principal strains are $\epsilon_1 = -\sigma_1/E$, $\epsilon_2 = -\nu\sigma_1/E$, $\epsilon_3 = -\nu\sigma_1/E$, where $\nu$ is Poisson's ratio. The fractional change in bulk volume and normalized density is:

$$\frac{\Delta V}{V} = \frac{\Delta \rho}{\rho} = \frac{\emptyset \Delta M_o}{M_o} = \epsilon_1 + \epsilon_2 + \epsilon_3 = (1 - 2\nu)\frac{\sigma_1}{E} \quad (5)$$

Since E has previously been determined and $\sigma_1$ is the known (measured) applied stress, X-ray CT measurements of $\Delta \rho/\rho$, or NMR measurements of $\Delta M_o/M_o$, allow for a determination of $\nu$ from equation 5. Alternatively, equations (3) and (5) may be combined so that the ratio of the slopes of fractional change in normalized density versus stress for uniaxial stress conditions ($S_u$) compared to hydrostatic stress conditions ($S_h$) may be employed to determine $\nu$ as follows:

$$\frac{S_u}{S_h} = (1 - 2\nu)/3 \quad (6)$$

Thus Poisson's ratio may be computed from:

$$\nu = 1/2 \left(1 - \frac{3S_u}{S_h}\right) \quad (7)$$

Under hydrostatic conditions the slope of fractional change in normalized density versus normalized axial shortening is unity, while under uniaxial conditions the slope of fractional change in normalized density versus normalized axial shortening is $(1-2\nu)$. This can be seen to be true from equation 5, where under uniaxial stress, the fractional change in volume and normalized density is:

$$\frac{\Delta V}{V} = \frac{\Delta \rho}{\rho} = (1 - 2\nu)\frac{\sigma_1}{E} \quad (8)$$

and the normalized axial shortening is:

$$\frac{\Delta l}{l} = \epsilon_1 = \sigma_1/E \quad (9)$$

so that the slope of fractional change in normalized density versus normalized shortening is $$\frac{(1 - 2\nu)\frac{\sigma_1}{E}}{\frac{\sigma_1}{E}} = (1 - 2\nu) \quad (10)$$

Further, two Lame's parameters $\lambda$ and G may also be determined from measurements of bulk compressibility $c_b$ and Poisson's ratio $\nu$, or from Poisson's ratio $\nu$ and Young's modulus E; these two Lame parameters completely determine the linear elastic properties of a material. Lame's parameters are defined in the theory of linear elasticity by:

$$\sigma_1 = (\lambda + 2G)\epsilon_1 + \lambda\epsilon_2 + \lambda\epsilon_3 \quad (11a)$$

$$\sigma_2 = \lambda\epsilon_1 + (\lambda + 2G)\epsilon_2 + \lambda\epsilon_3 \quad (11b)$$

$$\sigma_3 = \lambda\epsilon_1 + \lambda\epsilon_2 + (\lambda + 2G)\epsilon_3 \quad (11c)$$

where $\sigma_1$, $\sigma_2$, $\sigma_3$ are the principal stresses and $\epsilon_1$, $\epsilon_2$, $\epsilon_3$ are the principal strains. It can be shown (J. C. Jaeger and N. G. W. Cook, "Fundamentals of Rock Mechanics", John Wiley & Sons, Inc., N.Y., pps 110–111) that:

$$G = \frac{3(1 - 2v)}{2(1 + v)c_b} \quad (12a)$$

$$\lambda = \frac{3v}{(1 + v)c_b} \quad (12b)$$

and that:

$$G = \frac{E}{2(1 + v)} \quad (13a)$$

$$\lambda = \frac{Ev}{(1 + v)(1 - 2v)} \quad (13b)$$

and that:

$$G = \frac{3E}{9 - c_b E} \quad (14a)$$

$$\lambda = \frac{9 - 3Ec_b}{c_b(9 - Ec_b)} \quad (14b)$$

The foregoing analysis may also be extended to non-isotropic samples by using the appropriate directionally dependent moduli. In summary, the methods of the present invention are seen to determine a preselected mechanical or petrophysical property of a sample by employing an apparatus to image a region(s) of such a sample while applying preselected known forces to such a sample. In particular, the methods of the present invention image a region(s) of such a sample during application of known preselected hydrostatic and/or uniaxial forces to such a sample; from the hydrostatic forces, density and its changes may be determined which may then be combined with known or measured forces to determine bulk compressibility and/or Young's modulus and from the uniaxial forces, Poisson's ratio and Lame parameters may be determined from the known or measured uniaxial forces in conjunction with the hydrostatically determined properties. Further, the methods of the present invention completely determine the linear elastic properties of a material.

To illustrate the methods of the present invention for X-ray CT of various samples, the following examples are discussed. Although these examples employ the methods of the present invention over relatively large areas or regions of a sample, these methods may be employed over large or small regions, i.e. down to a pixel-sized region, of a sample.

A series of triaxial compression measurements were performed on outcrop specimens of Castlegate sandstone, employing the CT apparatus, described hereinbefore and a pressure vessel, also described hereinbefore in reference to FIG. 4. Table II lists the relevant sample properties. All the samples were cored from a single block and had the same orientation relative to the block (perpendicular to bedding). The samples were oven dried before any measurements were made. X-ray CT measurements were made by the X-ray scanner noted hereinbefore without any fluid in the pores to maximize the X-ray contrast between pore space and sand grains; saturating the pore space with brine or other liquids reduces the X-ray CT sensitivity by almost a factor of two. Nevertheless, such X-ray CT measurements may be made with liquid-saturated samples.

TABLE II

| Sample Properties | |
| --- | --- |
| Formation | Castlegate Sandstone Outcrop |
| Porosity | 30% |
| Air Permeability | 450 md |
| Diameter | 2 inch |
| Length | 4 inch |
| Uniaxial Compressibility | $0.4 \times 10^{-5}$/psi |
| Poisson's ratio | 0.2 |

For the measurements, the axial displacement (or strain) as well as the axial and radial pressures, of the sample in the pressure vessel 40 of FIG. 4 were measured continuously. The compaction examples were pressure (stress), rather than strain, controlled.

CT cross-sectional images were obtained by the CT scanner noted hereinbefore about every two minutes, at the center of the sample, as the pressure was increased in preselected, measured (known) increments. In addition, at various stages of the measurements, CT cross-sectional images were taken at 5 mm intervals along the entire length of the sample.

As an example, a compaction experiment is discussed hereinbelow. A sample was first loaded hydrostatically (via fluid 47 and fluid 49 of FIG. 4) to determine bulk compressibility and Young's modulus until a preselected maximum confining pressure was reached. As noted hereinbefore, the pressure was increased in known predetermined pressure increments with scanning occurring at the initial pressure and at the increased pressure. Alternatively, the initial pressure may be some high maximum pressure and then the pressure may be reduced in known predetermined pressure increments. Axial loading was then applied to determine Poisson's ratio until just before the sample failed, as indicated by the strain measurements. The axial pressure was then lowered slightly in order to carefully study the pre-failure deformation with the CT scanner. The typical duration of an experiment was about two hours.

Experiments were performed at confining pressures of 0, 500, and 1000 psi, resulting in failures at axial loads of 2250, 2750 and 8425 psi, respectively. All specimens failed in the brittle mode, as expected considering the low confining pressures used. No influence of the TEFLON endpieces on failure pressure was observed.

The deformational behavior of a sample having the sample properties listed in Table II loaded to the highest confining pressure (1000 psi) is displayed in FIGS. 5–7. FIG. 5 shows the normalized density change $\Delta\rho/\rho$, along the length of the sample. The density values were averaged in each cross-section every 5 mm along the core. Under hydrostatic pressure (i.e. the sample everywhere subjected to the same confining pressure), herein also called "hydrostat" or "hydrostatic", the CT data shows that the sample contracted relatively uniformly throughout its length (curve a). Table III shows that the bulk compressibility measured by CT under hydrostatic conditions agrees with the bulk compressibility measured from the axial shortening, demonstrating that compaction for this sample is isotropic along the hydrostat. This isotropic behavior is also consistent with the 45 degree slope (slope=1) of normalized density $\Delta\rho/\rho$ versus normalized axial shortening shown in FIG. 7.

Assuming linear elastic behavior, the bulk compressibility derived from hydrostatic compaction experiments should equal the bulk compressibility derived from uniaxial compaction experiments. In order to verify this, independent measurements were made on adjacent 35 mm specimens of Castlegate sandstone using a standard uniaxial compaction apparatus, such as those described in the Jager and Cook reference noted hereinbefore. The results are shown in FIG. 8. A third value of bulk compressibility can now be computed (neglecting grain compressibility) from the relation:

$$c_m = \tfrac{1}{3}[(1+\nu)/(1-\sigma)]c_b \quad (15)$$

where $\nu$ is Poisson's ratio, $c_m$ is the uniaxial compressibility, and $c_b$ is the bulk compressibility. For comparison with the hydrostatic measurements at 1000 psi, the value of $c_m$ used should correspond to a mean stress level of 1,000 psi which in the uniaxial experiment is reached at axial stress of 2,300 psi. A value for $c_b$ was calculated using a Poisson's ratio of 0.2 as found from CT measurements as described hereinbelow. The three measurements of bulk compressibility in Table III are in excellent agreement, showing again that the compaction of this sample is both linear and isotropic along the hydrostat. Alternatively, equation 15 may be employed to calculate $\nu$ when $c_m$, and $c_b$ are measured via an X-ray CT scanner or an NMR imaging apparatus, as noted hereinabove.

TABLE III

Values of Bulk Compressibility

From normalized axial shortening along hydrostat
$c_b = 0.36 \times 10^{-5}$/psi
From normalized density change (from CT) along hydrostat
(a) at center of sample
 $c_b = 0.32 \times 10^{-5}$/psi
(b) averaged over sample
 $c_b = 0.39 \times 10^{-5}$/psi
From uniaxial compaction measurements
$c_b = 0.4 \times 10^{-5}$/psi (for $\mu = 0.2$)

In the next stage of a compaction experiment, after hydrostatic loading to 1000 psi, the confining pressure was kept constant while the axial pressure was increased further. As shown in FIG. 5, (curve b) the deformation is now no longer uniform along the length of the sample. Instead, relative dilation occurs at the center of the core while at both ends compaction continues because the endpieces do not allow free radial movement of the sample during uniaxial loading. Care was taken to verify that this was not an artifact due to partial CT imaging of the endpieces. More specifically, the same effect was observed using TEFLON endpieces having a lower density than the sandstone, where partial imaging of the endpieces would have resulted in a deviation at the ends of the sample in the reverse direction from that which was observed.

A detailed picture of the compaction/dilation behavior at the center of the sample is given in FIGS. 6 and 7. FIG. 6 shows both the normalized density and axial shortening versus axial stress, while FIG. 7 is a crossplot of normalized density versus normalized axial shortening for the center slice of the sample of Table II. For linear elastic behavior, the slope (as noted hereinbefore in equation 10) in the uniaxial regime should be $(1-2\nu)$, which for a Poisson's ratio of 0.20, predicts a slope of 0.6. In FIG. 7, a slope of 0.6 is observed up to normalized axial shortening of about $7 \times 10^{-3}$. Nonlinear behavior begins for normalized axial shortening greater than this. The center density remains constant for values of $\Delta l/l$ between about 8 to $14 \times 10^{-3}$, because the compaction at the center is balanced by the radial dilatancy. For normalized axial shortening greater than about $14 \times 10^{-3}$, the normalized density at the center starts to decrease rapidly, resulting in failure at $\Delta l/l$ of about $15.5 \times 10^{-3}$.

Traditional measurements of total change in pore volume, which correspond to the normalized density from CT averaged over the entire sample, are represented by crosses (denoted "Avg.") in FIGS. 6 and 7. Because the sample compacted at the ends, these average density values differ considerably from the values in the middle of the core. Based on the average values, the rock appears compacted just before failure, whereas the center portion of the sample was in reality dilated. The deviation of the sample-averaged value of $\Delta \rho/\rho$ from the central portion value increases as the axial load is increased. Thus, end effects cause a systematic bias toward apparent compaction in all traditional data. The same behavior is observed even when TEFLON endpieces are used. This bias is even more severe at higher axial pressures.

The cross-sectional images of a center portion are shown in FIGS. 9A-9D corresponding to points A (zero pressure), B (1000 psi hydrostatic), C (just before fracture), and D (post-fracture) in FIG. 7. FIG. 9B shows the homogeneous composition of the specimen following hydrostatic loading. FIG. 9C shows the appearance of faint zones of increased porosity, the most distinct of which match with the fracture plane in FIG. 9D. The fracture plane coincides with some of the original zero-pressure higher porosity regions which suggests these were planes of weakness.

Using CT post-processing graphics software capable of zoom display, the density change in a specific area or region of a sample cross-section may be measured. This was done for each image in a small area (2.2 cm$^2$) chosen to include only the area of the future fracture. The average density change in the fracture area is plotted in FIG. 7 with open circles. The results for the fracture zone overlay those of the cross-sectional average in both the hydrostatic and dilatant regime, until just before fracture.

FIG. 10 summarizes the results of the experiments for the center portion of a sample at different confining pressures, as noted on the curves of this Figure. As the confining pressure is increased, the dilatancy is suppressed. At lower confining pressures multiple fractures developed upon failure.

Although the foregoing examples are for well consolidated materials, the methods of the present invention may also be employed on unconsolidated materials. In unconsolidated materials X-ray CT or NMR imaging is even more useful since density changes during compaction will typically be about ten times greater than in a consolidated sample. Further, NMR imaging may also be employed in the methods of the present invention, in a manner similar to the experiments noted hereinbefore.

Many other variations and modifications may be made in the techniques hereinbefore described, by those having experience in this technology, without departing from the concepts of the present invention. Accordingly, it should be clearly understood that the methods referred to in the foregoing description are illustrative only and are not intended as limitations on the scope of the invention.

What is claimed is:

1. A method for determining at least one preselected property of a sample of material employing an imaging apparatus comprising:

imaging said sample during the application of known preselected forces to said sample, and determining density in said sample responsive to said preselected forces.

2. The method of claim 1, wherein said known preselected forces comprise hydrostatic forces.

3. The method of claim 2, wherein said preselected property comprises porosity, bulk compressibility, bulk density, bulk volume, Young's modulus, or combinations thereof.

4. The method of claim 3, wherein said known preselected forces comprise uniaxial forces.

5. The method of claim 4, wherein said preselected property comprises Poisson's ratio, Lame parameters, or combinations thereof.

6. A method as described in claim 1, wherein said imaging apparatus employs electromagnetic radiation.

7. A method for measuring at least one mechanical property of a sample, comprising:

generating known preselected hydrostatic forces on said sample, imaging said sample during said generating of hydrostatic forces on said sample, and determining said property from average density and change in density between two different known hydrostatic forces and the average of said two known hydrostatic forces.

8. A method as described in claim 7, wherein said at least one mechanical property comprises: bulk compressibility, Young's modulus, or combinations thereof.

9. A method as described in claim 7, further comprising:

generating known preselected uniaxial forces on said sample, imaging said sample during said generating of uniaxial forces on said sample, and determining said property from average density and change in density between two different known uniaxial forces and the average of said two known uniaxial forces.

10. A method as described in claim 9, wherein said at least one mechanical property comprises: Poisson's ratio, Lame parameters, or combinations thereof.

11. A method for determining the onset of dilatant behavior for a sample in at least one region, comprising:

generating known uniaxial forces on said sample, imaging said sample in said at least one region during said generating of uniaxial forces on said sample, and determining the axial stress at which normalized density change versus axial stress first departs from linearity.

12. A method of measuring the size, shape, and location of a fracture inside a sample induced by applied forces, comprising:

generating forces sufficient to fracture said sample, imaging said sample before, during and after said generating of said forces, and constructing images of density inside said sample as a function of said forces.

* * * * *